(12) United States Patent
King et al.

(10) Patent No.: US 11,678,808 B2
(45) Date of Patent: *Jun. 20, 2023

(54) HAEMODYNAMIC DATA ESTIMATION APPARATUS AND METHOD OF USE

(71) Applicant: Bluedop Medical, Ltd., Nottingham (GB)

(72) Inventors: David H King, London (GB); Mohammed Al-Qaisi, Nottingham (GB)

(73) Assignee: Bluedop Medical, Ltd., Nottingham (GB)

(*) Notice: Subject to any disclaimer, the term of this patent is extended or adjusted under 35 U.S.C. 154(b) by 1099 days.

This patent is subject to a terminal disclaimer.

(21) Appl. No.: 15/403,760

(22) Filed: Jan. 11, 2017

(65) Prior Publication Data

US 2017/0181642 A1 Jun. 29, 2017

Related U.S. Application Data

(63) Continuation-in-part of application No. 13/138,622, filed on Feb. 2, 2012, now Pat. No. 10,966,617.

(30) Foreign Application Priority Data

Mar. 13, 2009 (GB) .................................. 0904435
Mar. 11, 2010 (WO) ............... PCT/GB2010/000436

(51) Int. Cl.
*A61B 8/00* (2006.01)
*A61B 5/021* (2006.01)
(Continued)

(52) U.S. Cl.
CPC ............. *A61B 5/021* (2013.01); *A61B 8/06* (2013.01); *A61B 5/02007* (2013.01); *A61B 5/055* (2013.01)

(58) Field of Classification Search
CPC ..... A61B 5/02007; A61B 5/021; A61B 5/055; A61B 8/06; A61B 8/488
See application file for complete search history.

(56) References Cited

U.S. PATENT DOCUMENTS 5,139,020 A  8/1992  Koestner et al.
5,188,105 A  2/1993  Keimel
(Continued)

FOREIGN PATENT DOCUMENTS

EP  1715428 A1  10/2006
EP  3636146 A1   4/2020
(Continued)

OTHER PUBLICATIONS

Buyens et al., "Calculation of Left Ventricle Relative Pressure Distribution in MRI using Acceleration Data", Magnetic Resonance in Medicine (Year: 2005).*

(Continued)

*Primary Examiner* — Christopher L Cook
(74) *Attorney, Agent, or Firm* — Dentons US LLP (57) ABSTRACT

A system and method for deriving information on disease in vascular segments for example mean pressure, drop in mean pressure and/or hydraulic resistance, from such measured waveforms is described. The waveforms can, for example, be measured non-invasively using Doppler ultrasound or magnetic resonance techniques. Form Factors (Vff, Pff) for the velocity waveform and the central arterial pressure are determined. Lesions may be detected and located using the estimated non-invasive hemodynamic information.

11 Claims, 6 Drawing Sheets

(51) Int. Cl.
  *A61B 8/06* (2006.01)
  *A61B 5/055* (2006.01)
  *A61B 5/02* (2006.01)

(56) References Cited

U.S. PATENT DOCUMENTS

| | | | |
|---|---|---|---|
| 5,409,010 A * | 4/1995 | Beach | A61B 8/06 600/455 |
| 5,533,511 A | 7/1996 | Kaspari et al. | |
| 6,007,491 A | 12/1999 | Ling et al. | |
| 6,251,077 B1 | 6/2001 | Mo et al. | |
| 6,733,449 B1 | 5/2004 | Krishnamurthy et al. | |
| 2004/0013292 A1 | 1/2004 | Raunig | |
| 2004/0186379 A1 | 9/2004 | Landry et al. | |
| 2004/0243006 A1 | 12/2004 | Nakata et al. | |
| 2005/0119569 A1 | 6/2005 | Ohtake | |
| 2005/0137479 A1 | 6/2005 | Haider | |
| 2005/0156593 A1 | 7/2005 | Assmann et al. | |
| 2007/0123779 A1 | 5/2007 | Hoctor et al. | |
| 2007/0293760 A1 | 12/2007 | Schaafsma | |
| 2008/0015451 A1 * | 1/2008 | Hatib | A61B 5/0215 600/481 |
| 2008/0027330 A1 | 1/2008 | Naghavi et al. | |
| 2008/0114255 A1 | 5/2008 | Schwartz et al. | |
| 2008/0132769 A1 | 6/2008 | Henderson et al. | |
| 2009/0088626 A1 | 4/2009 | Sutton et al. | |
| 2010/0081941 A1 | 4/2010 | Naghavi et al. | |
| 2010/0198062 A1 | 8/2010 | Everett et al. | |
| 2010/0331688 A1 | 12/2010 | Baba | |
| 2011/0066041 A1 | 3/2011 | Pandia et al. | |
| 2012/0123246 A1 | 5/2012 | King et al. | |
| 2013/0281862 A1 | 10/2013 | Yoon et al. | |
| 2014/0358000 A1 | 12/2014 | Gupta et al. | |
| 2017/0181642 A1 | 6/2017 | King et al. | |
| 2021/0052246 A1 | 2/2021 | King et al. | |

FOREIGN PATENT DOCUMENTS

| | | | |
|---|---|---|---|
| JP | 2001-95803 A | 4/2001 | |
| JP | 2003-70758 A | 3/2003 | |
| JP | 2005-81081 A | 3/2005 | |
| WO | 2001021057 A2 | 3/2001 | |
| WO | 2007012809 A2 | 2/2007 | |
| WO | 2007056386 A2 | 5/2007 | |
| WO | 2009/013287 A1 | 1/2009 | |
| WO | 2019135096 A1 | 7/2019 | |
| WO | 2022/038364 A1 | 2/2022 | |

OTHER PUBLICATIONS

Dan et al., "Cerebral Blood Flow Velocity Declines Before Arterial Pressure in Patients with Orthostatic Vasovagal Presyncope", J. American College of Cardiology (Year: 2002).*
Sesso et al., "Systolic and Diastolic Blood Pressure, Pulse Pressure and Mean Arterial Pressure as predictors of Cardiovascular Disease Risk in Men", Hypertension (Year: 2000).*
Nakayama et al., "Ascending fractional pulse pressure closely relating to large artery function", J. of Human Hypertension (Year: 2002).*
EPO Communication pursuant to Rules 161 issued for EP Application No. 18708730.9 dated Sep. 11, 2020; (3 Pages).
International Preliminary Report on Patentability issue in PCT Application No. PCT/IB2018/00000047 dated Jul. 7, 2020, (7 Pages).
International Search Report and Written Opinion Issued in PCT Application No. PCT/IB2018/000047 dated Sep. 12, 2018 (11 Pages).
Scheinfield et al., "Understanding the Spectral Doppler Waveform of the Hepatic Veins in Health and Disease," RadioGraphics 2009, vol. 29, No. 7, pp. 2081-2099.
Tehan et al., "Use of hand-held Doppler ultrasound examination by podiatrists; a reliability study," Journal of Foot and Ankle Research, 2015, (7 Pages).
USPTO Final Office Action in U.S. Appl. No. 15/353,862 dated Dec. 23, 2020, (15 Pages).
USPTO Non-Final Office Action in U.S. Appl. No. 15/353,862, dated Mar. 27, 2020, (14 pages).
Wennberg, "Approach to the Patient with Peripheral Arterial Disease," American Heart Association, downloaded from http://ahajournals.org on Mar. 23, 2020 (10 Pages).
PCT International Search Report and Written Opinion in PCT International Application Serial No. PCT/GB2010/000436 dated Jun. 10, 2010.
PCT International Preliminary Report on Patentability in PCT International Application Serial No. PCT/GB2010/000436 dated Sep. 13, 2011.
Dan Dan et al: "Cerebral blood flow velocity declines before arterial pressure in patients with orthostatic vasovagel presyncope." Journal of the American College of Cardiology, vol. 39, No. 6, Mar. 20, 2002, pp. 1039-1045, XP02583383 ; ISSN: 0735-1097, p. 1039-1040.
Leotta et al. "Display of Spatially-registered Doppler spectral waveforms and three-dimensional vein graft geometry," Ultrasound in Medicine and Biology, vol. 31, No. 10, Oct. 31, 2005, pp. 1317-1326, XP005150232 ISSN: 0301-05629.
De Morais Filho et al: "Segmental Waveform Analysis in the Diagnosis of Peripheral Arterial Occlusive Diseases," Annals of Vascular Surgery, vol. 18, No. 6, Nov. 1, 2004, pp. 714-724, XP005941393 ISSN: 0890-5096 the whole document.
Formaggia et al., "The Circulatory System; from case studies to mathematical modeling," 2006 available online at http://link.springer.com/chapter/10.1007/88-470-0396-2-7.
Evans et al., "The Relationship between Ultrasonic Pulsatility index and Proximal Arterial Stenosis in a Canine Model," Apr. 1980.
Huppert et al., "A multicompartment vascular model for interferring baseline and functional changes in cerebral oxygen metabolism and arterial dilation," Journal of cerebral Blood flow and metabolism, 2007.
Pressure-Flow Characteristics of Coronary Stenoses in Unsedated Dogs at Rest and during Coronary Vasodilation; K. Lance Gould; Circulation Research; vol. 43, No. 2, pp. 242-253, Aug. 1978 (12 Pages).
R. Nave "Current Law and Flowrate," Available online Jan. 26, 2000, Wayback Screen Shot Feb. 19, 2008, http://link.springer.com/chapter/10.1007TF88-470-036962_7.
Online Viscosity Measurement of Complex Solutions Using Ultrasound Doppler Velocimetry; Volkan Koeseli et al., Turk J Chem, 30 (2006) pp. 297-304 (8 Pages).
Thompson et al., "Real-Time Volumetric Flow Measurements with Complex-Difference MRI;" NIH Public Access, Author Manuscript; Magn Reson in Med. Dec. 2003; 50(6) 1248-1255; (8 Pages).
Hong GI Li, et al., "Fourier Transformation of Arterial Doppler Waveforms of the Lower Extremity," Journal of Clinical Ultrasound, vol. 32, No. 6, Jul./Aug. 2004, (pp. 277-285).
Post Exercise Doppler Blood Velocity Patterns in Health and Disease; D.H. King et al., published more than 1 year prior to the priority date of the present application (2 Pages).
Grundlagen der Dynamic des Arterienpulses, Wetterer E and Kenner Th, Springer-Verlag, Berlin, 1968; Chapter 8, Incident and incoming waves (Translated from the German Text) (8 Pages).
Bohorquez et al., "An integrated-circuit switched capacitor model and implementation of the Heart," Oct. 2008, pp. 1-5.
An in vivo study of the total occlusion method for the analysis of forward and backward pressure waves; D.L. Newman et al., Cardiovascular Research, 1979, 12, pp. 595-600 (6 Pages).
Strategies for Rapid NMR Rheometry by Magnetic Resonance Imaging Velocimetry; Stephen J. Gibbs et al., Journal of Magnetic Resonance 125, pp. 43-51, 1997 (9 Pages).
Japanese Office Action issued in Japanese Application No. 2020-537513, dated Aug. 16, 2022, with English Summary.
Japanese Office Action issued in Japanese Application No. 2020-537513, dated Oct. 19, 2021, with English Translation.
Non-Final Office Action issued in U.S. Appl. No. 13/138,622, dated Feb. 6, 2015.
Non-Final Office Action issued in U.S. Appl. No. 15/353,862, dated Oct. 13, 2021.

(56) References Cited

OTHER PUBLICATIONS

Final Office Action issued in U.S. Appl. No. 15/353,862, dated Jun. 6, 2022.
Notice of Allowance issued in U.S. Appl. No. 13/138,622, dated Feb. 2, 2021.
Notice of Allowance issued in U.S. Appl. No. 13/138,622, dated Dec. 9, 2020.
Final Office Action issued in U.S. Appl. No. 13/138,622, dated Sep. 15, 2015.
Non-Final Office Action issued in U.S. Appl. No. 13/138,622, dated Aug. 15, 2016.
Final Office Action issued in U.S. Appl. No. 13/138,622, dated Apr. 19, 2017.
Non-Final Office Action issued in U.S. Appl. No. 13/138,622, dated Mar. 8, 2018.
Final Office Action issued in U.S. Appl. No. 13/138,622, dated Sep. 12, 2018.
Non-Final Office Action issued in U.S. Appl. No. 13/138,622, dated May 17, 2019.
Non-Final Office Action issued in U.S. Appl. No. 16/959,417, dated Sep. 29, 2021.
Notice of Allowance issued in U.S. Appl. No. 16/959,417, dated Apr. 13, 2022.
International Search Report dated Nov. 23, 2021 for PCT/GB2021/052157 filed Aug. 19, 2021.
Written Opinion of the International Searching Authority PCT/GB2021/052157 dated Nov. 23, 2021.

* cited by examiner

FIG. 8 ns, much as hydraulic circuits are controlled by control systems. Hemodynamie response continuously monitors and adjusts to conditions in the body and its environment. Thus, hemodynamics explains the physical laws that govern the flow of blood in the blood vessels, The relationships can be challenging because blood vessels are complex, with many ways for blood to enter and exit under changing conditions.

HAEMODYNAMIC DATA ESTIMATION APPARATUS AND METHOD OF USE

CROSS REFERENCE TO RELATED APPLICATIONS

This application is a continuation-in-part of U.S. patent application Ser. No. 13/138,622 filed on Feb. 2, 2012, which is a National Stage Application of Patent Cooperation Treaty Application Number PCT/GB2010/000436 filed on Mar. 11, 2010 and entitled Haemodynamic Data Estimation, which claims priority from UK Intellectual Property Office application number 0904435.5 filed on Mar. 13, 2009,entitled Haemodynamic Data Estimation, the entire disclosure of each of which is incorporated herein by reference.

STATEMENT REGARDING FEDERALLY SPONSORED RESEARCH OR DEVELOPMENT

N/A

JOINT RESEARCH AGREEMENT

N/A

STATEMENT REGARDING PRIOR DISCLOSURES BY THE INVENTOR OR A JOINT INVENTOR

N/A

BACKGROUND OF THE INVENTION

Field of the Invention

The present invention relates to Blood Pressure Monitoring and Analysis Devices and more particularly pertains to a unique HEMODYNAMIC DATA ESTIMATION APPARATUS AND METHOD OF USE for providing a non-invasive real-time or near-real-time estimate of mean blood pressure for almost any arterial location in a normal or diseased, exercised or resting mammalian arterial network provided a representative Central Reference Blood Pressure is included.

Description of the Prior Art

The use of Blood Pressure Monitoring and Analysis Devices is known in the prior art. More specifically, Blood Pressure Monitoring and Analysis Devices heretofore devised and utilized are known to consist basically of familiar, expected and obvious structural configurations. Illustrative examples of known prior art include the 293 following:

U.S. Pat. No. 6,007,491 issued to Ling et al. on 28 Dec. 1999;

US Pub No.2005/0119569A1 by Ohtake Published on 2 Jun. 2005;

US Pub No.2007/0293760A1 by Schaafsma Published on 20 Dec. 2007;

US Pub No.2008/0027330A1 by Naghavi et al. Published on 31 Jan. 2008;

US Pub No. 2010/0198062A1 by Everett et al. Published on 5 Aug. 2010

SUMMARY OF THE INVENTION

Background Information

Hemodynamics is the fluid dynamics of blood flow. The circulatory system is controlled by homeostatic mecha- The heart is the driver of the circulatory system, pumping blood through rhythmic contraction and relaxation. The rate of blood flow out of the heart (often expressed in L/min) is known as the cardiac output (CO).

Blood being pumped out of the heart first enters the aorta, the largest artery of the body. It then proceeds to divide into smaller and smaller arteries, then into arterioles, and eventually capillaries, where oxygen transfer occurs. The capillaries connect to venules, and the blood then travels back through the network of veins to the right heart. The microcirculation—the arterioles, capillaries, and venules—constitutes most of the area of the vascular system and is the site of the transfer of $O_2$ glucose, and enzyme substrates into the cells. The venous system returns the de-oxygenated blood to the right heart where it is pumped into the lungs to become oxygenated and $CO_2$ and other gaseous wastes exchanged and expelled during breathing. Blood then returns to the left side of the heart where it begins the process again.

For the purposes of explanation and illustration, and not for purposes of limitation, some of the concepts related to the physiological functions related to blood flow may be related in terms of mathematical terms. These mathematical terms are not the subject of the present invention itself, but rather are used to provide a reference framework from which the present invention may be better understood by those who are skilled in the art, as well as those who are not.

In a normal circulatory system, the volume of blood returning to the heart each minute is approximately equal to the volume that is pumped out each minute (the cardiac output). Because of this, the velocity of blood flow across each level of the circulatory system is primarily determined by the total cross-sectional area of that level. This is mathematically expressed by the following equation:

$$v=Q/A$$

where
v=velocity (cm/s)
Q=blood flow (ml/s)
A=cross sectional area ($cm^2$)

The blood pressure in the circulation is principally due to the pumping action of the heart. The pumping action of the heart generates pulsatile blood flow, which is conducted into the arteries, across the micro-circulation where oxygen is transferred to the tissues and eventually, back via the venous system and the lungs to the heart. During each heartbeat, systemic arterial blood pressure varies between a maximum (systolic) and a minimum (diastolic) pressure. In physiology these are often simplified into one value, the mean arterial pressure (MAP), which is calculated as follows:

$$MAP=\tfrac{2}{3}(BP_{dia})+\tfrac{1}{3}(BP_{sys})$$

Note: $BP_{dia}$ weighted more heavily since the heart spends two thirds of the heart beat cycle in the diastolic.

where:
MAP=Mean Arterial Pressure
$BP_{dia}$=Diastolic blood pressure
$BP_{sys}$=Systolic blood pressure Instantaneous differences in mean blood pressure are responsible for blood flowing from one location to another in the circulatory system. The pressure required to drive mean blood flow depends on the resistance to flow presented by the transit arteries, being principally controlled by pre-capillary valves(sphincters) which in turn are driven by metabolic needs. Mean blood pressure decreases as the circulating blood moves away from the heart through arteries arterioles and capillaries due to viscous losses of energy. Gravity affects static blood pressure via hydrostatic forces (e.g., during standing) but has little effect on blood flow. Respiration and pumping from contraction of skeletal muscles combined with venous valves action assist the return of deoxygenated blood to the Right side of the heart, then to the lungs and finally back to the Left side of the heart.

A stenosis is an abnormal narrowing of a blood vessel. A stenosis may be caused by atherosclerosis, diabetes, calcification, infection, birth defects, or smoking. An occlusion is a blockage of a blood vessel which is usually bypassed by smaller caliber 'collateral' arteries, Stenoses and occlusions are collectively termed vascular disease. The presence of stenoses or occlusions result in an abnormally elevated resistance in the supply artery however The effect on blood flow caused by increased resistance in the transit arteries resulting from either by a stenosis or an occlusion is opposed by the 'auto-regulatory' control of the pre capillary sphincters which control flow through the microcirculation in order to prevent tissue perfusion pressure dropping to a dangerously low level. In extreme cases auto-regulation fails, perfusion pressure drops precipitously, capillaries collapse, blood flow ceases and tissue becomes starved of oxygen. Although the relationship between tissue perfusion pressure and abnormal arterial resistance is a complex one, knowledge of perfusion pressure is known to be useful in understanding the physiology and pathology associated with the mammalian vascular system.

With the preceding as background information, the present invention provides a system and method for deriving information on disease in vascular segments through non-invasive means using Doppler ultrasound.

Before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DESCRIPTION OF PREFERRED EMBODIMENTS

With reference now to the drawings, and in particular to FIGS. 1 through 6 thereof, a new HEMODYNAMIC DATA ESTIMATION APPARATUS AND METHOD OF USE embodying the principles and concepts of the present invention and generally designed by the reference numeral 10 will be described.

The present invention relates to a system and method for estimating hemodynamic data, in particular although not exclusively to non-invasively obtaining in vivo mean pressure within the normal and diseased segments of the vascular system.

With human life expectancy increasing worldwide the effects of progressive arterial disease become more apparent within the aging population. This disease commonly takes the form of stenosis (localized cross sectional arterial narrowing) which may represent a significant resistance to blood flow in, for instance, the iliac and femoral arteries, the popliteal artery, the peroneal artery, or the tibial arteries resulting in claudication. The effect of a stenosis on resistance is nonlinear, causing symptoms when narrowing exceeds a threshold value.

Where narrowing completely obscures the arterial cross section the stenosis becomes an occlusion, In what follows a stenosis or an occlusion will be used interchangeably where permitted by the context and will be referred to collectively as 'disease' or 'a lesion'.

In order to gauge the clinical significance of individual lesions, local hemodynamic information needs to be obtained.

Downstream blood pressure and pressure drop across a lesion have been shown to be sensitive indicators of stenotic disease but prior to the present invention this could only be assessed in the limbs employing occlusive cuff methods or elsewhere in the vascular system by invasive insertion of pressure catheters directly into the vascular system. Unfortunately occlusive cuffs are problematic for the 30% of patients with calcified vessels, as they are not accurate. Pressure catheters are not feasible for screening due to their invasive nature.

It would be desirable to derive an indirect measure of disease magnitude that is non-invasive and doesn't rely on a pressure cuff. Aspects of the present invention are set out in the independent claims. Further, optional features are defined in the dependent claims.

For the purposes of explanation and illustration, and not for purposes of limitation, some of the concepts related to the physiological functions related to blood flow may be related in terms of mathematical terms. These mathematical terms are not the subject of the present invention itself, but rather are used provide a reference framework from which the present invention may be better understood by those who are skilled in the art, as well as those who are not.

Embodiments of the present invention provide a system and method for deriving information or data on a lesion based on a form factor of wave forms derived non-invasively using measured physiological data such as blood velocity or flow rates and pressure supplying a specific vascular bed, that is the vascular vessels and tissues of an organ or muscle), under examination. These embodiments are based on the realization that simple form factor measures extracted from measured velocity and pressure data can be used to estimate 1. The ratio between upstream and downstream resistance pertaining to a specific measurement location/vascular bed (e.g. brain, kidney, muscle).
2. Estimate local absolute mean blood pressure perfusing that vascular bed.
3. Locate lesions within the vascular pathway supplying a specific vascular bed.

DESCRIPTION OF THE DRAWINGS

Embodiments of the invention are now described by way of example only and with reference to the accompanying drawing in which.

Figure 1:
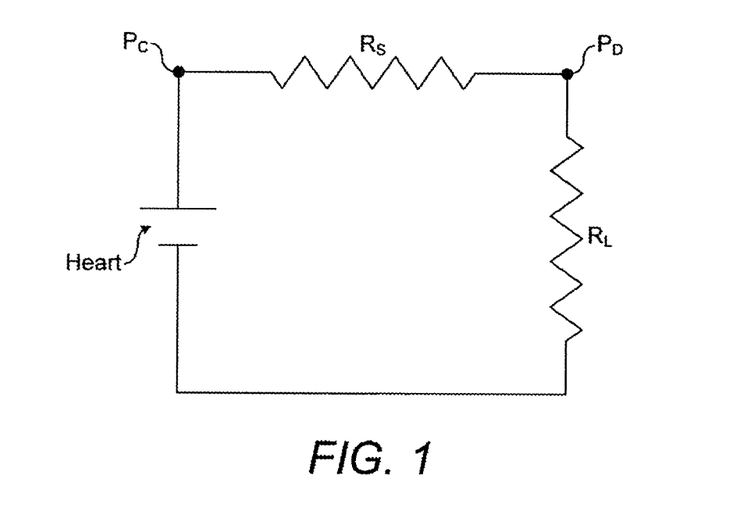
FIG. 1 illustrates a he adynamic model informing the present invention.

With reference to FIG. 1, a simplified hemodynamic model of a mammalian vascular system comprises a driving element corresponding to the heart, a source resistance RS corresponding to the internal resistance of the heart and the resistance of the transit arteries carrying blood to the vascular beds, a vascular segment or segment of vasculature represented by the load resistance RL which also includes the resistance of the veins closing the circuit to the heart. The heart generates a variable flow rate at a constant pressure PC, which flows through the transit arteries represented by RS. This generates a pressure drop across RS, finally perfusing the vascular bed at a pressure PD. The venous component of the resistance and pressure drop across RL is small under physiological conditions (with the venous blood pressure being much lower than the central and peripheral blood pressures, the former being of the order of less than 10 mmHg and the latter being of the order of 100 mmHg). The pressure PD and resistance RL can therefore, to a first approximation, be taken as being characteristic of the peripheral bed under investigation. It should be noted that in the case of an arterio-venous fistula created for dialysis the venous side becomes arterialised and in this special case the return pathway via superficial vein to deep vein can be considered as the arterial supply in the model described below.

The distal mean pressure PD is related to the central mean pressure PC by $$PD = PC/(1+RS/RL) \qquad \text{equation 1}$$

where RS is the internal heart and transit artery resistance and RL is the vascular bed resistance of the tissue under investigation, both in units of PRU, that is mmHg/ml per minute and the pressures are in units of mmHg. Thus it can be seen that, based on a simple hemodynamic pressure divider model, peripheral blood pressure can be calculated from central blood pressure, if both the source and load resistances are known or can be measured. However, it is precisely the lack of knowledge of these quantities, which is one aspect of the problems addressed by embodiments described herein.

It has previously be shown that, in the matched state when by definition RS=RL, the incident pressure and resultant velocity waveforms in a circuit similar to the one shown in FIG. 1 are of the same shape and not distorted because any capacitive and inductive effects (arterial compliance and blood mass in this analog) are eliminated (see Orundlagen der Dynamic des Arterienpulses, Wetterer E and Kenneth Th, Springer-Verlag Berlin, 1968). In this matched state, the ratio RS/RL used in the calculation of PD above is unity.

Underlying the described embodiments, is the realization that given the similarity of flow and pressure waveforms shown previously, the ratio of a form factor descriptive of the shape of the pressure and velocity waveforms should equally be unity and that it may be possible to generalise this correspondence between a ratio of resistances and a ratio of form factors across a range of resistances outside the matched state to provide a measurable quantity which can be used to estimate peripheral or distal pressure (PD) at any point around the vascular circuit from the left side of the heart (arterial) to the right side (venous).

Figure 2:
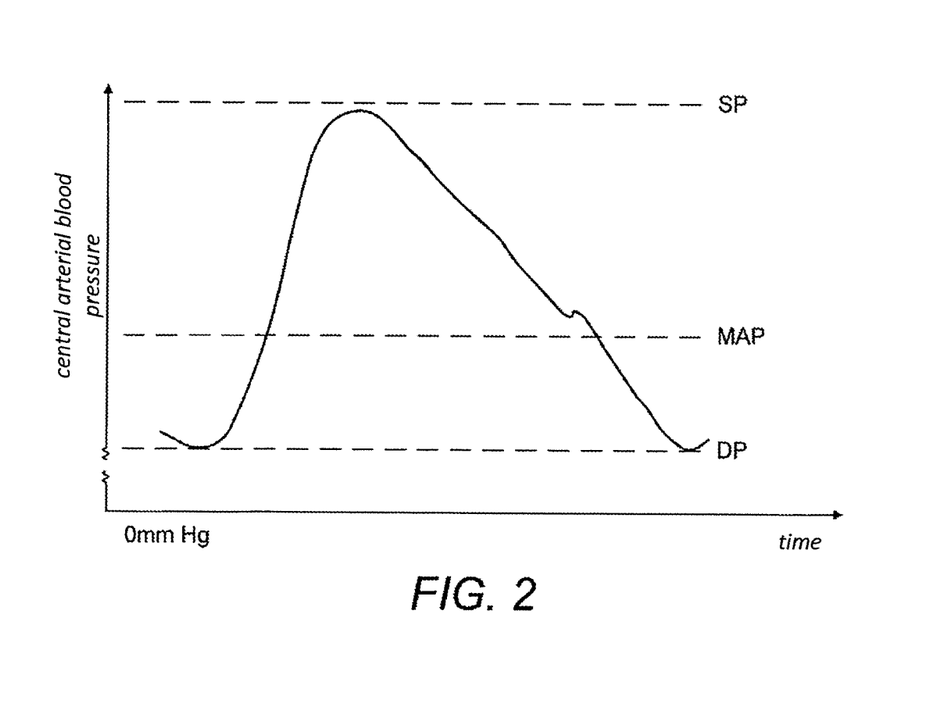
FIG. 2 illustrates an example central arterial blood pressure/time waveform including AC and DC terms.

One Form Factor describing the AC term of the pressure waveform relative to the DC level is the ratio of the pulse pressure (systolic or peak pressure minus diastolic or lowest pressure) relative to the mean pressure, averaged over one heart beat. A central arterial pressure wave is shown in FIG. 2, illustrating Systolic Pressure (SP), Mean Arterial Pressure (MAP) and Diastolic Pressure (DP) and the zero pressure reference datum. In the matched state, the velocity/time and pressure/time waveform will be of the same shape. In the present description, the Form Factor (ff) for the central arterial pressure is termed Pressure form factor (Pff), such that Pff=(SP−DP)/MAP and the form factor for the velocity waveforms measured in the periphery is termed Velocity form factor (Vff), such that Vff=(Vmax−Vmin)/ V mean. It should be noted that the flow/time waveform will be identical in shape to the velocity/time waveform. Therefore the argument (below) applies to a corresponding flow/time form factor (Fff) calculated from a flow/time waveform, as well. In the remainder, a reference to Vff is understood to include reference to Fff, context permitting.

In the matched state, because the pressure/time and velocity/time waveform shapes are identical, the ratio of their form factors will be identical. Thus Pff/Vff=1. But RS/RL=1 in the matched state so that by substituting either RS/RLor Pff/Vff in equation 1, the identical result is obtained such that PD=PC/2.

Underlying the described embodiments is the realization that this relationship may hold not only in the matched states but generally, Examining an upper limit for the distal pressure when RL is infinite under total peripheral vasoconstriction, RS/RL=0. In this state the DC velocity(flow) term approaches zero and therefore Vff also approaches infinity, thus Pff/Vff=0. Substituting, RS/RLor Pff/Vff in equation 1, the identical result is obtained such that PD=PC.

Similarly, when the peripheral bed is bypassed, for example with an a-v fistula as used in dialysis, RL, approaches zero and therefore RS/RL approaches ∞. Similarly Vff approaches zero because the DC velocity component becomes very much larger than the AC component of the velocity/time waveform. Therefore Pff/Vff approaches ∞. Substituting either RS/RL or Pff/Vff in equation 1, the identical result is obtained such that PD=0.

The above theoretical considerations show that at 3 points over the range from peripheral bed bypass to total peripheral vasoconstriction, with the matched state occurring in between these two, the ratio RS/RL can be replaced with a ratio of form factors as Pff/Vff. This suggests the following formula for calculating PD:

$$PD = PC/(1+Pff/Vff) \qquad \text{equation 2}$$

Similarly, the pressure drop between the source and the load is given by:

$$PC-PD = PC/(1+Vff/Pff) \qquad \text{equation 3.}$$

A number of assumptions underlie the derivation of the above relationship, which are now listed in as much as they have not been discussed above:

1) Pff and Vff are always finite
2) Pff central pressure=Pff incident pressure The accuracy of this assumption can be validated in a number of ways (see below).
3) The subject is supine. Otherwise any difference in hydrostatic pressure between the measurement of central blood pressure (e.g. using a brachial cuff) and the location of the measurement of the velocity waveform can be taken account of by a correction of $\Delta P = (h[\text{centimeter}]/13.6)$ [mmHg].
4) The incident pressure stems from the left ventricle. If this is not the case, for example for measurements in pulmonary or hepatic arteries, blood pressure waveforms would need to be measured directly with a catheter based pressure transducer, Only one determination needs to be made, unless changes in Pff are expected to occur.
5) Arterial characteristics are assumed to be constant over a heart beat. This does not apply to coronary arteries where the dynamic change of the transit arteries and vascular bed due to the mechanically compression during the cardiac cycle makes this quantity time varying. However, as long as Pff is measured directly the same equation should be valid
6) The above model assumes that the waveform underlying the calculation of Vff is measured at the termination of the supply to the vascular bed under test.

Figure 3A:
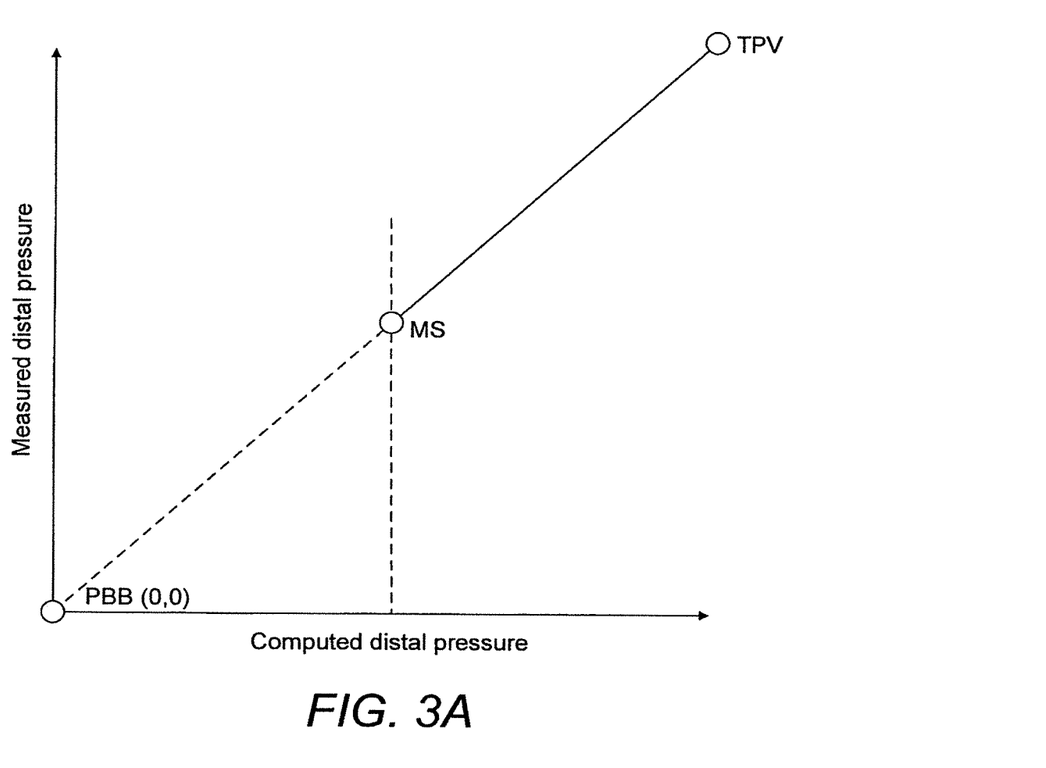
FIG. 3A illustrates a relationship between measured distal mean pressure and distal mean pressure computed in accordance with described embodiments.

The above discussion of an expression for calculating peripheral pressure based on mean central pressure and a ratio of measures of shape of central pressure and peripheral velocity waveforms has been based on a theoretical analysis of the behavior of these quantities at Total Peripheral Vasoconstriction (TPV), the Matched State (MS) and Peripheral Bed Bypass (PBB). The result is further supported by experimental data now described with reference to FIG. 3A. FIG. 3A schematically depicts experimental data obtained from canine experiments plotting computed distal pressure based on the expression described above against measured distal pressure, together with the PBB, MS and TPV states discussed above. Experimental data was only obtained between the MS and TPV regimes but a straight line fit to that data indicates that the relationship between the measured distal pressure and computed distal pressure has a slope of one and a y intercept approaching the origin, as can be expected based on the above theoretical discussion.

Experimental Confirmation of the Theory is Described Below

The in vivo experiment involved a canine model. Pressure sensing catheters having side facing pressure sensors were advanced to the femoral artery of the 15 kg greyhound. A directional Doppler ultrasound was placed over the surgically exposed femoral artery allowing Doppler velocity spectral data to be recorded. A pressure sensitive catheter was also placed in the aorta allowing heartbeat to heartbeat measurements of systolic pressure, diastolic pressure, and mean pressure. From this the form factor $P_{ff}$ was calculated. Pressure/time waveforms were recorded from the femoral artery pressure catheter giving an actual measurement of distal pressure, $P_D$ for comparison. From the Doppler probe on the femoral artery, blood velocity/time spectral waveforms were recorded which allowed tracking of $V_{max}$, $V_{min}$, and $V_{mean}$ pulse by pulse, enabling the calculation of the velocity form factor, $V_{ff}$ for each individual cardiac cycle.

Figure 3B:
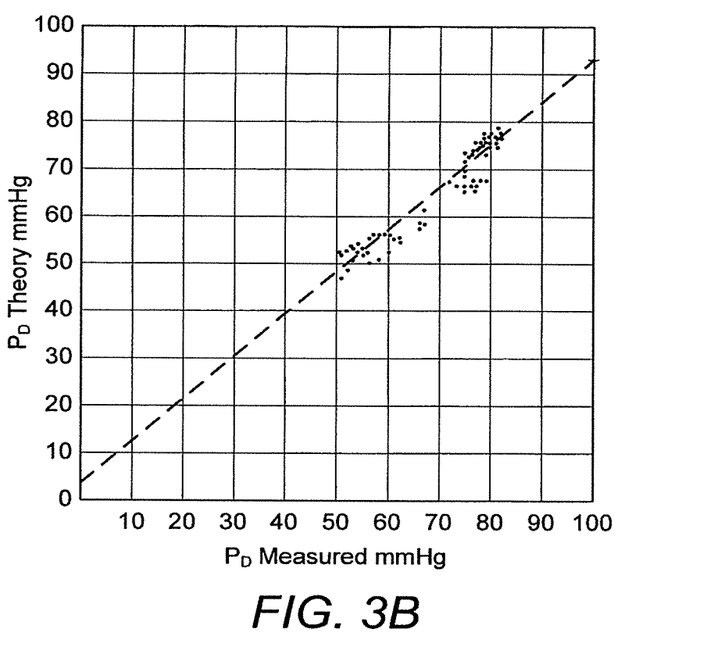
FIGS. 3B and 3C show corresponding experimental data.

First the dynamic hyperemic response was simulated. After 1 minute of iliac artery compression resulting in total occlusion the compression was released. A range of $P_D$ values were recorded as blood flow peaked then returned to resting state. FIG. 3B shows $P_D$ values as measured with the pressure sensing catheter on the x-axis. The calculated $P_D$ values from the Doppler measurements of velocity were plotted on the y axis. Straight line fit display data had a slope of 0.885 with a y-intercept at 3.04 mmHg and a correlation coefficient of 0.962.

Figure 3C:
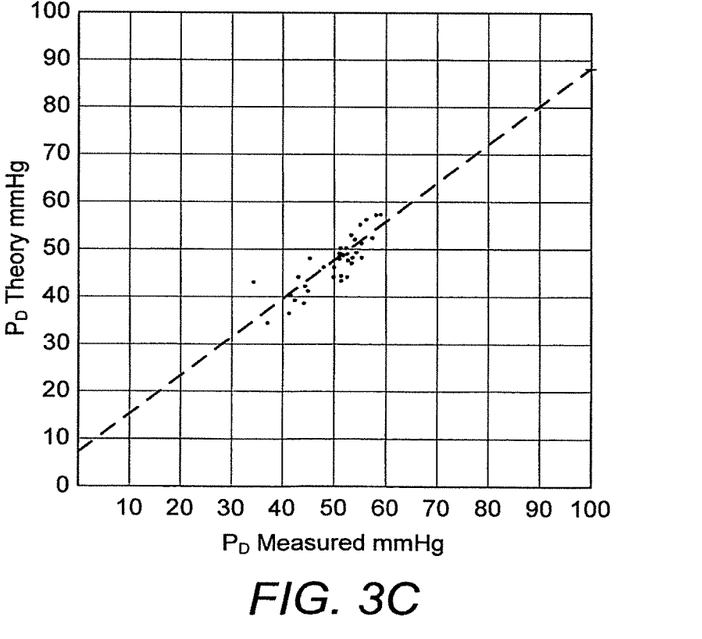
Figure 4:
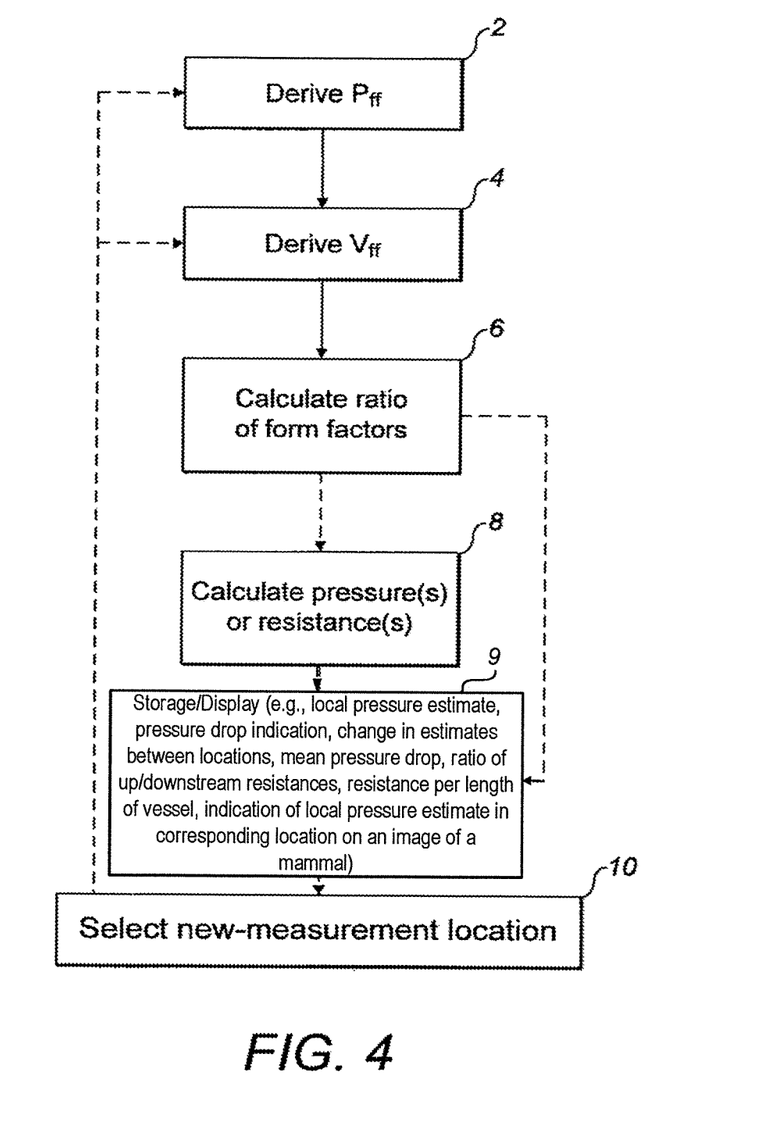
FIG. 4 is a flow diagram illustrating steps of described embodiments.
Figure 5:
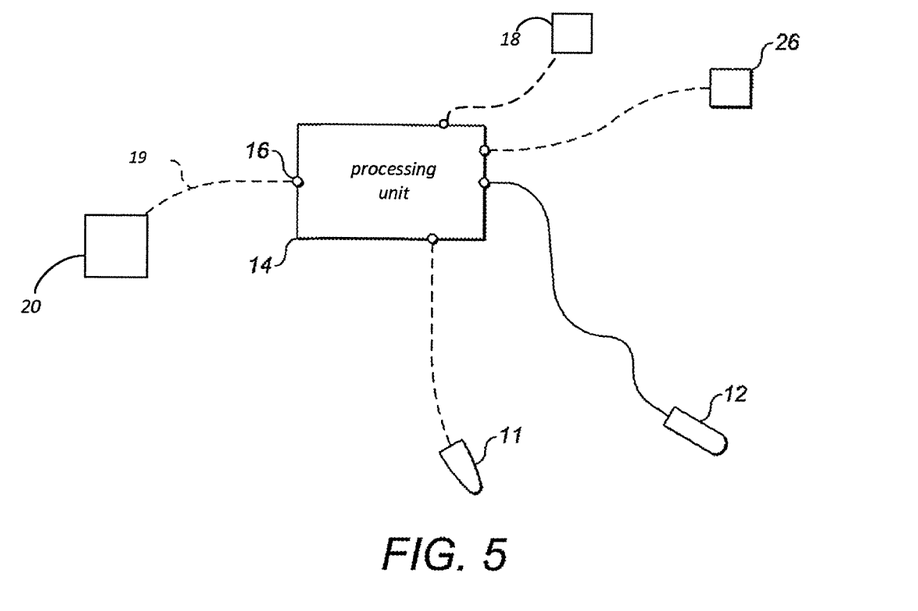
FIG. 5 illustrates ultrasound-based embodiments.

Second a range of pulse by pulse measurements were made at a resting state during partial degrees of manual compression of the iliac artery. $P_{ff}$, $V_{ff}$, $P_C$, and $P_D$ were then calculated for each cardiac cycle. FIG. 3C shows $P_D$ values as measured with the pressure sensing catheter on the x-axis. The calculated $P_D$ values form the Doppler measurements of velocity were plotted on the y axis. Straight line fit display data had a slope of 0.795 with a y intercept at 7.31 mmHg and a correlation coefficient of 0.836

Assumptions

A number of assumptions underlie the derivation of the above relationship, which are now listed in as much as they have not been discussed above:

1) $P_{ff}$ and $V_{ff}$ are always finite.
2) Pff brachial pressure=Pff central pressure=$P_{ff}$ incident pressure
3) The subject is supine, otherwise a correction for height difference must be employed:

$\Delta P = (h[\text{centimeter}]/13.6)$ [mmHg]

4) If an elevated Central Venous Pressure (CVP) is present and known, a correction can be carried out such that CVP is subtracted from Mean Arterial Pressure when calculating Pff such that:

$$P_{ff} = \frac{SP - DP}{(MAP - CVP)} \qquad \text{Equation 4}$$

5) Arterial characteristics are assumed to be constant over a heartbeat.
6) Where estimation of the perfusion pressure supplied to a specific vascular bed, $V_{ff}$ is measured just proximal to the vascular bed under test.

By sampling at various points along the supply pathway the presence of a lesion between the last two sampling points will be signaled by an abrupt change in the computed pressures, resistances or ratios (of form factors or resistances).

In accordance with the model discussed above when the sampled volume is moved from upstream to downstream of a lesion within the arterial supply pathway $P_D$ and $R_L$ drop markedly and $P_C$-$P_D$ and $R_S$ rises markedly. In some embodiments, where only a single measurement is taken, an abnormally high value of $R_S$ (or $P_C$-$P_D$) indicates a lesion or stenosis upstream and an abnormally high value or $R_L$ (or $P_D$) indicates a lesion or stenosis downstream of the measurement point One specific application of $P_D$ would be the ability to establish the presence, due to disease, of critically low perfusion pressures in isolated organs (typically less than 30 mmHg).

Historically, ankle/brachial pressure index (ABI) has been used as a convenient indicator of clinically significant peripheral arterial disease in the lower limbs. Systolic pressure can be simply obtained by placing a CW Doppler device over the artery immediately downstream of an encompassing pressure cuff. When the cuff is inflated to equal or just exceeds the systolic blood pressure within the artery, the audio signal from the Doppler device will cease. By recording the cuff pressure at that precise moment, the intra-arterial systolic pressure is assumed to be equal the cuff pressure. To obtain an ABI, an arm and an ankle blood pressure cuff are applied. in the presence of one or more clinically significant lesions within the arteries supplying the lower limbs, the ratio between ankle/arm systolic pressures falls below a pre-established threshold value.

With the realization that mesa pressure may be used in place of systolic pressure such that the ratio between ankle and arm pressure may be used to signal the presence of a hemodynamically significant lesion or lesions involving the arterial blood supply to the lower limbs, the following application is suggested. The method uses mean arm blood pressure recorded using the auscultation methods described above, from which Pff may be calculated. With Pff known, ankle pressure can be estimated (for instance), from CW Doppler blood velocity spectral waveforms obtained from the posterior tibial artery. By employing the theory described above, the calf pressure cuff is eliminated, and an analogous diagnostic ratio (ABIm) is computed such that;

$$ABIm = \frac{\text{Ankle mean pressure}}{\text{Brachial mean pressure}} = \frac{P_D}{P_C} = \frac{1}{\left(1 + \frac{P_{ff}}{V_{ff}}\right)} \quad \text{Equation 5}$$

The resulting ratio may be compared with a pre-established threshold. This alternative diagnostic method offers several advantages (for instance), by avoiding measurement problems caused by artificial elevation of ankle cuff systolic pressures in diabetic subjects and allowing an assessment to be made where open wounds, medical dressings or a plaster cast prevents the application of an ankle pressure cuff.

It will be understood that the above description is made by way of example only and of embodiments of the invention to further the understanding of the invention and is not intended to be limiting.

Figure 6:
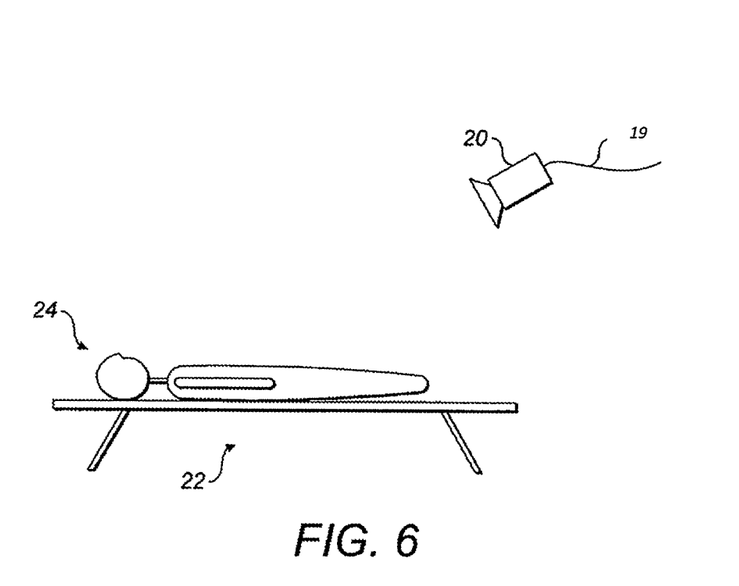
FIG. 6 illustrates an embodiment of the functional hardware blocks of the present invention.
Figure 7:
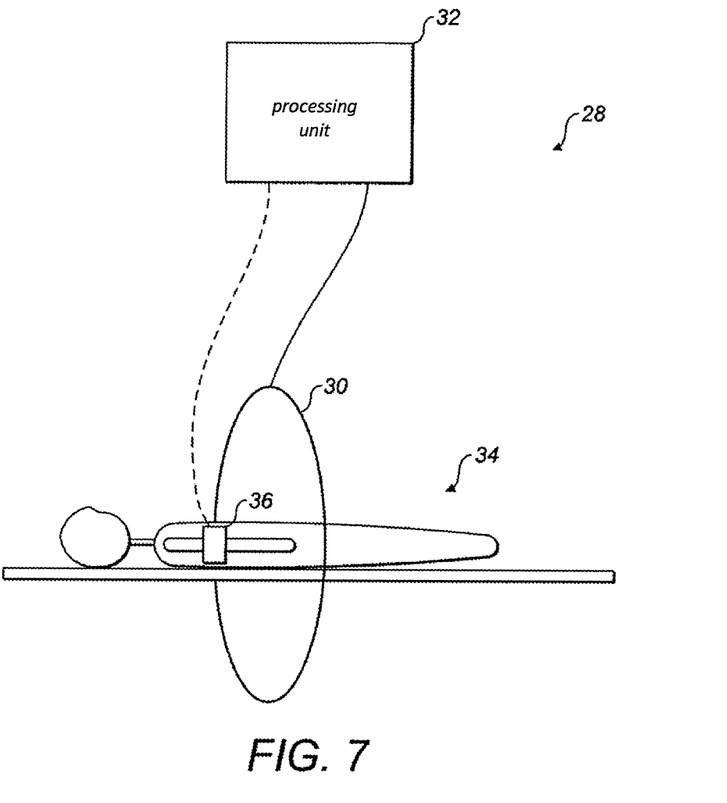
FIG. 7 illustrates an MRI-based embodiment.
Figure 8:
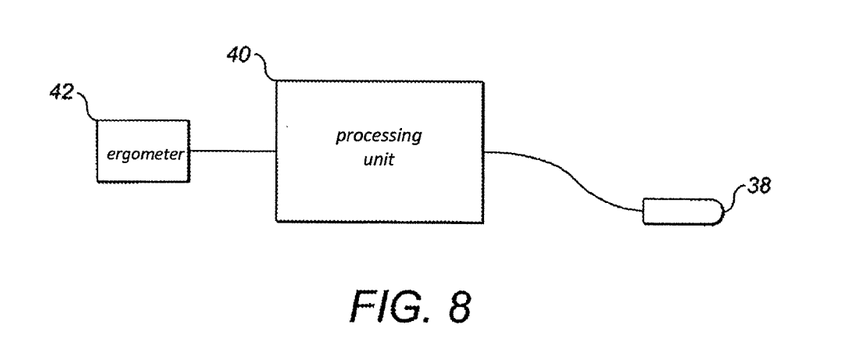
FIG. 8 illustrates a system for estimating maximum energy output of a subject.

As an illustrative example of the current invention, and without departing from the scope of the previous illustrative embodiments the present invention may also be considered to comprise a waveform capture assembly 20, a waveform converter and processor 30 and a Display 50. as shown in FIG. 6.

In at least one preferred embodiment, the waveform capture assembly is a non-invasive apparatus such as a Continuous Wave Doppler ultrasound ("CW" Doppler"). In alternative embodiments the waveform capture assembly could also be a Duplex Doppler ultrasound or a Magnetic Resonance Imaging ("MRI") system. For purposes of illustration and not limitation an implementation using a CW Doppler system will be further described. The waveform capture assembly 20 may include a Doppler probe 22 and a Doppler transceiver 24. The Doppler probe is placed against the skin of the subject immediately adjacent to the Primary Location of interest and captures a set of Doppler baseband shifted audio signals received back from the blood flowing through blood vessel located at the Primary Location. It should be understood that there may be a single Primary Location of interest or a plurality of Primary Locations along a specific vascular pathway. The Doppler transceiver 24 preferably converts the signals received from the Doppler Probe 22 to a baseband version and transmits the audio baseband version to the Waveform Converter and Processor 30. The Waveform Converter and Processor 30 then uses the baseband version of the captured Doppler shifted data to determine relative Maximum blood Velocity, relative Minimum blood Velocity and relative Mean blood Velocity for each cardiac cycle yielding a Vff reading for each cardiac cycle. Vff is non dimensional parameter, therefore it can be seen that Doppler shift values may be used in place of scaled Velocity values. This simplifies the acquisition of Doppler shifted blood velocity data by eliminating the need for probe/vessel angle to be known as is required when. Absolute blood velocity is required. Thus all Velocity Values quoted here are unsealed Relative blood velocity values, The Waveform Capture Assembly may be connected to the Waveform Converter and Processor by hard-wire, wireless communication, or an intermediate device. Optionally the coordinates of the waveform capture assembly over the region of interest may be recorded (for example) by video tracking a LED light mounted on the tip of a CW Doppler probe.

The Waveform Converter and Processor 30 is a physical device which provides real time spectral analysis, filtering, gain control, and statistical processing of the processed Doppler shifted data. This may be implemented as an all hardware solution, or as a hardware device which implements specific functions through software controlled processors. It should also be understood that for at least the purposes of this illustrative embodiment, that the waveform converter and processor is operationally coupled to a "real time" visual display 50 of the Doppler shifted blood velocity waveform. Baseband audio sounds are provided to aid the operator in finding the appropriate blood vessel and optimizing the received signal.

As described more fully above, a Reference (Arm) Blood Pressure, including a maximum ("Systolic") pressure and a minimum ("Diastolic") pressure of the subject is provided to the Waveform Converter and Processor 30. The Reference Systolic and Diastolic Blood Pressure data is considered to be constant from minute to minute and is therefore sampled only once per measurement session. Systolic and Diastolic blood pressure values may be input manually, be provided automatically by an operationally coupled electronic sphygmomanometer 26, or through other automated means. A simple algorithm, known in the 'art' may be used to estimate the mean arterial pressure (MAP). Alternatively automatic sphygmomanometers designed to provide MAP readings from oscillometric information may be used, providing all three required parameters without requiring an additional process. In any case a single reference Pff value is provided to the Waveform Converter immediately prior to any measurement session The Waveform converter and Processor 30 then determines a number of parameters associated with both the Reference Blood Pressure arid the Relative Blood Velocity data. A preferred method for determining these parameters is described over the next several paragraphs and illustrative examples are included in the following tables.

With regard to the Reference Blood Pressure a Mean value for the arterial pressure (MAP) for one cardiac cycle may be calculated as the sum of the product of two thirds times the Diastolic plus the product of one third times the Systolic blood pressure. A "Second Measure" is then determined by calculating the difference between the Systolic blood pressure minus the Diastolic blood pressure the result then being divided by the Mean blood pressure.

Similarly, a "First Measure" is then determined by calculating the difference between the relative Maximum blood Velocity minus the relative Minimum blood Velocity with the resulting sum then being divided by the relative Mean blood velocity. It can be seen that the 'First Measure is a linear dimensionless quantity and therefore maximum, minimum and mean values do not need to be scaled in terms of absolute velocity. Unlike MAP, mean blood Velocity cannot be estimated from maximum and minimum velocity data. Instead it needs to be computed by a waveform converter and processor that is operationally coupleable to the waveform capture assembly.

To calculate the pressure at the First location $P_D$, the central pressure, $P_C$, is divided by the sum of the ratio of the second measure to the first measure and one (see equation 2).

For purposes of illustration and not limitation, the following tables present three different Reference Blood Pressures (One for each table) and five Estimated blood Pressures for the Primary Location based upon a range of examples of Relative Maximum, Minimum and Mean blood Velocities. It is important to note that these tables provide illustrative examples of the determining process and are not intended to be indicative on anticipated results for any condition or situation.

Sample Calculations

TABLE 1 sample calculation performed with a Right ArmBP of 120/80 mmHg and various representative distal velocity measurements

| | | | | | |
|---|---|---|---|---|---|
| Systolic Pressure$_{mmHg}$ | 120 | 120 | 120 | 120 | 120 |
| Diastolic Pressure$_{mmHg}$ | 80 | 80 | 80 | 80 | 80 |
| Central Mean Pressure $P_C = \frac{1}{3}P_{sys} + \frac{2}{3} * P_{dia}$ mmHg | 93 | 93 | 93 | 93 | 93 |
| Second Measure, $P_{ff} = (P_{sys} - P_{dia})/P_{mean}$ | 0.43 | 0.43 | 0.43 | 0.43 | 0.43 |
| Maximum Velocity | 100 | 100 | 80 | 60 | 40 |
| Minimum Velocity | −30 | −10 | 10 | 20 | 30 |
| Mean Velocity | 15 | 25 | 35 | 40 | 35 |
| First Measure, $V_{ff} = (V_{max} - V_{min})/V_{mean}$ | 8.67 | 4.40 | 2.00 | 1.00 | 0.29 |
| $P_D = P_C/(1 + P_{ff}V_{ff})$ mmHg | 89 | 85 | 77 | 65 | 37 |
| ABIm | 0.95 | 0.91 | 0.82 | 0.70 | 0.40 |

TABLE 2 sample calculation performed with a Right ArmBP of 160/80 mmHg and various representative distal velocity measurements

| | | | | | |
|---|---|---|---|---|---|
| Systolic Pressure$_{mmHg}$ | 160 | 160 | 160 | 160 | 160 |
| Diastolic Pressure$_{mmHg}$ | 80 | 80 | 80 | 80 | 80 |
| Central Mean Pressure $P_C = \frac{1}{3}P_{sys} + \frac{2}{3} * P_{dia}$ mmHg | 107 | 107 | 107 | 107 | 107 |
| Second Measure, $P_{ff} = (P_{sys} - P_{dia})/P_{mean}$ | 0.75 | 0.75 | 0.75 | 0.75 | 0.75 |
| Maximum Velocity | 100 | 100 | 80 | 60 | 40 |
| Minimum Velocity | −30 | −10 | 10 | 20 | 30 |
| Mean Velocity | 15 | 25 | 35 | 40 | 35 |
| First Measure, $V_{ff} = (V_{max} - V_{min})/V_{mean}$ | 8.67 | 4.40 | 2.00 | 1.00 | 0.29 |
| $P_D = P_C/(1 + P_{ff}V_{ff})$ mmHg | 98 | 91 | 78 | 61 | 29 |
| ABIm | 0.92 | 0.85 | 0.73 | 0.57 | 0.28 |

TABLE 3 sample calculation performed with a Right Arm BP of 100/60 mmHg and various representative distal velocity measurements

| | | | | | |
|---|---|---|---|---|---|
| Systolic Pressure$_{mmHg}$ | 100 | 100 | 100 | 100 | 100 |
| Diastolic Pressure$_{mmHg}$ | 60 | 60 | 60 | 60 | 60 |
| Central Mean Pressure $P_C = \frac{1}{3}P_{sys} + \frac{2}{3} * P_{dia}$ mmHg | 73 | 73 | 73 | 73 | 73 |
| Second Measure, $P_{ff} = (P_{sys} - P_{dia})/P_{mean}$ | 0.55 | 0.55 | 0.55 | 0.55 | 0.55 |
| Maximum Velocity | 100 | 100 | 80 | 60 | 40 |
| Minimum Velocity | −30 | −10 | 10 | 20 | 30 |
| Mean Velocity | 15 | 25 | 35 | 40 | 35 |
| First Measure, $V_{ff} = (V_{max} - V_{min})/V_{mean}$ | 8.67 | 4.40 | 2.00 | 1.00 | 0.29 |
| $P_D = P_C/(1 + P_{ff}V_{ff})$ mmHg | 69 | 65 | 58 | 47 | 25 |
| ABIm | 0.94 | 0.89 | 0.79 | 0.65 | 0.34 |

As will now be readily apparent to those skilled in the art, while the present invention provides a significant advantage over invasive techniques for a single location, it can also be used to determine the absolute mean arterial pressure from multiple arterial locations in real time. This allows the operator to rapidly determine the location of and extent of a lesion or stenosis, providing incredible benefit and utility over the prior art.

In still a further embodiment, the display may provide a graphic representation of any segment of the vascular structure of interest along with a near-real-time estimate of Blood pressure associated with the portion of the vascular segment currently being evaluated.

In still a further embodiment, a visual or audio indicia is provided to the user when a significant discontinuity in the estimate of Blood Pressure occurs thereby providing the user with an indication of the location of a lesion.

It will be understood that the above description is made by way of example only and of embodiments of the invention to further the understanding of the invention and is not intended to be limiting. Many modifications, variations, combinations and juxtapositions of the embodiments described above will be apparent to a person skilled in the art and are intended to be covered by the scope of the appended claims.

The above derivation is based on the realization that a ratio of measures indicative of shape of central blood pressure and local blood velocity or blood flow waveforms can be used to replace the ratio of resistances in the standard hemodynamic pressure divider equation. The above discussion has been centered on the particular example of a Form Factor index, as defined above. However, other measures are equally envisaged to be used in place of the Form Factor used in the described embodiments, as will be apparent to the skilled person. Such measures may include the Fourier coefficient of the first component of a normalized Fourier transform of the waveforms or any other measure of determining the shape of the waveforms, specifically those which are indicative of the relative contribution of the AC and DC components of the waveforms.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A system comprising:
   a blood pressure measurement device for measuring a reference blood pressure of a mammal at a reference location in a vascular system of the mammal, the reference blood pressure comprising a systolic pressure and a diastolic pressure, the measurements collectively being the reference blood pressure;
   a waveform capture assembly capturing a representation of a velocity waveform of blood flow at an interest location in the vascular system of the mammal by focusing the waveform capture assembly at the interest location on the mammal;
   a waveform converter and processor operationally coupled to the waveform capture assembly and the blood pressure measurement device, the waveform converter and processor receiving the reference blood pressure of the mammal, analyzing the captured representation of the velocity waveform of blood flow to identify a plurality of parameters associated with the waveform and the reference blood pressure, and estimating a local blood pressure at the interest location; and
   a display operationally coupled to the waveform converter and processor for providing at least one visual indicia for a user based on the estimate of local blood pressure, facilitating disease detection,
   wherein estimating the local blood pressure at the interest location comprises:
      calculating a central mean pressure as being a sum of two thirds of the diastolic reference blood pressure plus one third of the systolic reference blood pressure,
      determining a first measure from the plurality of parameters identified in the analyzed blood flow velocity waveform,
      determining a second measure based on the difference between the reference systolic blood pressure and the reference diastolic blood pressure divided by the calculated central mean blood pressure value, and
      calculating an estimate of the mean blood pressure for the interest location by the steps of:
         dividing the second measure by the first measure for an intermediate value;
         adding one to the intermediate value for a second intermediate value; and
         dividing the calculated central mean blood pressure by the second intermediate value, yielding an estimate of mean blood pressure at the interest location.

2. The system of claim 1, wherein the waveform capture assembly is selected from the group of waveform capture devices consisting of continuous wave (CW) Doppler ultrasound, duplex Doppler ultrasound, and magnetic resonance imaging (MRI).

3. The system of claim 1, wherein the waveform converter and processor determines the estimate of local blood pressure by the steps of:
   determining a relative maximum blood velocity from a single cardiac cycle from the waveform capture assembly and associated with the interest location;
   determining a relative minimum blood velocity from the same cardiac cycle from the waveform capture assembly and associated with the interest location;
   determining a relative mean blood velocity from the same cardiac cycle and associated with the interest location;
   determining the first measure from the difference between the relative maximum velocity and the relative minimum velocity, divided by the relative mean velocity taken from the single cardiac cycle and associated with the interest location.

4. The system of claim 1, wherein the estimate of mean blood pressure for the interest location is presented to a user on the display in real time or near real time.

5. The system of claim 4, wherein the anatomical position of the interest location is captured by tracking and recording a current position of the waveform capture device.

6. The system of claim 5, wherein a plurality of waveform representations of blood flow each from a known anatomical location of interest on a subject is captured by the waveform capture assembly and an estimate of the mean blood pressure for each interest location at a known position is determined by the waveform converter and processor.

7. The system of claim 6, wherein a visual representation of a vascular segment of interest between any two selected interest locations is provided for a user on the display along with a corresponding indicia representing the estimated mean blood pressure difference between the two selected interest locations.

8. The system of claim 7, further comprising:
   a visual indicia corresponding with a threshold change in the estimates of mean blood pressure difference for that segment compared with pressure differences recorded within the associated proximal and distal segments in order to indicate the presence of a significant lesion with reference to its location relative to a surface anatomy of the subject.

9. The system of claim 8, whereby a non-invasive estimate hemodynamic resistance between any two selected interest locations distal to the reference pressure location is provided to the user.

10. The system of claim 9, wherein a color indicia associated with a discontinuity in estimate hemodynamic resistance, between two or more of the plurality of points along the selected segment is displayed.

11. The system of claim 1, wherein the interest location is distal from the reference location of the reference blood pressure.

* * * * *